(12) United States Patent
Jackson et al.

(10) Patent No.: US 6,607,488 B1
(45) Date of Patent: Aug. 19, 2003

(54) MEDICAL DIAGNOSTIC ULTRASOUND SYSTEM AND METHOD FOR SCANNING PLANE ORIENTATION

(75) Inventors: John I. Jackson, Menlo Park, CA (US); John A. Hossack, Charlottesville, VA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/517,014

(22) Filed: Mar. 2, 2000

(51) Int. Cl.[7] .................................................. A61B 8/00
(52) U.S. Cl. ........................................ 600/443; 600/466
(58) Field of Search .......................... 600/437, 443–447, 600/459–467, 424, 471; 128/916; 607/122

(56) References Cited

U.S. PATENT DOCUMENTS

| | | | |
|---|---|---|---|
| 5,054,942 A | * | 10/1991 | Scribner et al. ............. 600/462 |
| 5,207,225 A | * | 5/1993 | Oaks et al. .................. 600/463 |
| 5,415,175 A | | 5/1995 | Hanafy et al. |
| 5,538,004 A | | 7/1996 | Bamber |
| 5,563,810 A | | 10/1996 | Cherry et al. |
| 5,596,990 A | * | 1/1997 | Yock et al. .................. 600/462 |
| 5,633,494 A | | 5/1997 | Danisch |
| 5,728,044 A | | 3/1998 | Shan |
| 5,797,849 A | | 8/1998 | Vesely et al. |
| 5,876,345 A | | 3/1999 | Eaton et al. |
| 5,928,151 A | | 7/1999 | Hossack et al. |
| 5,984,869 A | | 11/1999 | Chiao et al. |
| 6,014,473 A | | 1/2000 | Hossack et al. |
| 6,248,075 B1 | * | 6/2001 | McGee et al. .............. 600/463 |

OTHER PUBLICATIONS

Transom Technologies, Inc., Transom Corporate Overview; pp. 1–5.

* cited by examiner

*Primary Examiner*—Francis J. Jaworski
*Assistant Examiner*—Ali M. Imam

(57) ABSTRACT

A method and system for indicating the position and orientation of a scan plane relative to a patient is provided. The image as presented on a display is oriented in accordance with the orientation of a transducer. The orientation may provide for displaying an image where the transducer is not in a transducer up or transducer down position, but is rotated away from vertical of the display. Alternatively or additionally, a two or three-dimensional graphical generic representation is provided with a scan plane indicated as a polygon or image rendering within a generic representation to show relative positioning of the scan plane with respect to the patient.

89 Claims, 7 Drawing Sheets

MEDICAL DIAGNOSTIC ULTRASOUND SYSTEM AND METHOD FOR SCANNING PLANE ORIENTATION

BACKGROUND

This invention relates to a medical diagnostic ultrasound system and method for scan plane orientation. In particular, graphics, annotation, and/or ultrasound image orientation for visualizing the location and orientation of a scan plane within a patient are provided.

Ultrasound images represent anatomical structure within a body. As typically displayed, the ultrasound image is oriented with respect to the transducer such that the portion of the image closest to the transducer is on the top or bottom of the display. Some ultrasound systems allow the user to flip from a transducer up to a transducer down position or vice versa. Minimal operator controls may also be included to allow the operator to flip the image left and right. Regardless of how the orientation of the transducer with respect to the patient changes during the course of an exam, the image orientation is restricted to the transducer up or transducer down orientation. The position of the scan plane with reference to the anatomical structure shown on the ultrasound image is difficult to determine. As a result, the image is difficult to interpret, such as for interpretation by someone not controlling the transducer.

Other medical Imaging methodologies, such as computed tomography (CT) or Magnetic Resonance Imaging (MRI) provide images oriented on the display relative to the body being imaged. For example, transverse or nearly transverse images are presented with the anterior portion of the anatomy at the top, the posterior portion of the anatomy on the bottom, the left portion of the anatomy on the right and the right portion of the anatomy on the left. Coronal or nearly coronal images are presented with the superior portion of the anatomy on the top, the inferior portion on the bottom, the right portion on the left and the left portion on the right. As yet another example, sagittal images are positioned with the superior portion of the anatomy on the top and the inferior portion of the anatomy on the bottom.

Information indicating the orientation of the image with respect to the transducer has been provided for some ultrasound applications. For example, images generated with a transesophageal transducer use icons to indicate the position of the transducer array with respect to the transducer housing. A transverse or a longitudinal icon, such as the letters "T" or "L", may be displayed with an image to indicate which of the two transducer planes within the transesophageal transducer are in use. For a multi-plane transesophageal transducer, an angle icon indicating the rotation of the transducer within the probe is provided.

Ultrasound systems have also provided an outline of a torso or head on a display. A dash is then positioned relative to the outline to represent where the transducer was located for obtaining an image displayed on the display in the traditional manner described above.

U.S. Pat. No. 5,797,849 describes tracking various objects within a patient's body, and imaging the objects as well as the anatomical structure. At column 30, lines 43–50, Vesely et al. describe positioning a pie shaped sector scan into a 3-D scene of the patient. A perspective rendering of a patient frame of reference based on scanning the patient, the location and direction of surgical instruments, and the pie shaped image are then oriented within the scene as shown in FIG. 18 of that patent. FIG. 18 of that patent shows the pie shaped ultrasound sector image in a transducer up position. The 3-D scene appears to have been oriented around the vertically positioned pie shaped sector.

U.S. Pat. No. 5,876,345 also discloses information indicating the placement of the scanned plane relative to the patient's body. In particular, a transducer up image such as shown in FIGS. 10, 12 and 13 of that patent is shown generated with a linear transducer array. An icon representing a sector as well as a numerical display indicates the position of the two-dimensional image relative to the body. The two-dimensional linear image is statically positioned. FIGS. 11, 12 and 13 of that patent also show a image generated with a radial array of transducer elements on a catheter. The radial image is designated by a circular border or edge with the position of the transducer indicated as a center point. At column 10, lines 30–33, Eaton et al. disclose rotating the radial image display according to the detected rotation angle to compensate for the physical device or transducer rotation. However, the result is different placement of the anatomical structure within the circular image without any change in the placement of the border or the edge of the image.

BRIEF SUMMARY

The present invention is defined by the following claims, and nothing in this section should be taken as a limitation on those claims. By way of introduction, the preferred embodiment described below includes a method and system for displaying ultrasound images. The image is oriented on the display in a manner consistent with the orientation of the anatomy, allowing a physician to more easily interpret the content of the image and relative positions of anatomical structures. The image is rotated away from the "transducer up" position such that a line orthogonal to the transducer face is displayed at an angle away from vertical position on the display. As used herein, the transducer-up position corresponds to an image generated as if the transducer were on the top of the scan plane.

Alternatively or additionally, the relative position of the scan plane and associated image relative to the body is represented by positioning a generic representation of the body relative to the image. For example, the images are displayed in a transducer up or transducer down position, and a wire frame or other representation, such as a three-dimensional wire frame representation, is positioned to indicate the location of the scan plane within the body.

Such orientation information is particularly advantageous for images generated from an array internal to the body. Orienting the image on the display in association with the relative position on the scan plane within the patient may also be valuable for surgeons or other physicians not accustomed to viewing ultrasound images. Likewise, such oriented images allow for more efficient comparison with images generated using other modalities, such as CT or MRI. The image representing anatomical structure may also be displayed with a generic representation of a portion of the body, such as a torso, portion of the torso or an organ, to allow better orientation and relative position determination by the user.

In a first aspect, an improvement is provided for a medical diagnostic ultrasound two-dimensional image representing a two-dimensional region within a body and comprising an edge having at least one point corresponding to a position substantially adjacent to a transducer. The improvement includes orienting the image such that a direction orthogonal to a center of a face of the transducer is at an angle of rotation away from vertical on the display.

In a second aspect, a medical diagnostic ultrasound method for displaying a two-dimensional image is provided. A two-dimensional ultrasound image is generated. The two-dimensional ultrasound image is oriented such that the image appears rotated from a transducer up or down position as a function of the border of the image.

In a third aspect, a medical diagnostic ultrasound system is provided for displaying a two-dimensional image. An ultrasound transducer probe is adapted for use external to a patient to scan a two-dimensional region of the patient. A display is operable to display an ultrasound two-dimensional image representing the two-dimensional region wherein the display is free of three-dimensional representations rendered as a function of a scan of the patient. A controller is operative to orient the two-dimensional image as a function of an angle of the transducer probe relative to the patient.

In a fourth aspect, a medical diagnostic ultrasound method and system for imaging a region of a body are provided. A transducer ultrasonically scans a region of interest in the body. An orientation of the region with respect to anatomical features of the body is monitored, such as with a position sensor or other device. A display displays an ultrasound two-dimensional image responsive to the scan and displays a generic representation of at least a portion of the body wherein the image is geometrically aligned with the generic representation.

Further aspects and advantages of the invention are discussed below in conjunction with the preferred embodiments.

DETAILED DESCRIPTION OF THE PREFERRED EMBODIMENTS

An ultrasound image is displayed with information conveying the geometric orientation of the scan plane within the patient's body. For example, the image is oriented such that a direction orthogonal to a center of a face of a transducer is oriented at an angle of rotation away from vertical on the display (i.e., the ultrasound image is rotated from a transducer up or transducer down position on the display). As another example, numerical or other labels are provided indicating a position of the image relative to the patient's body. As yet another example, the image is displayed with a generic representation where the image and the generic representation are aligned to represent a position of the scan plane within the body.

Figure 1:
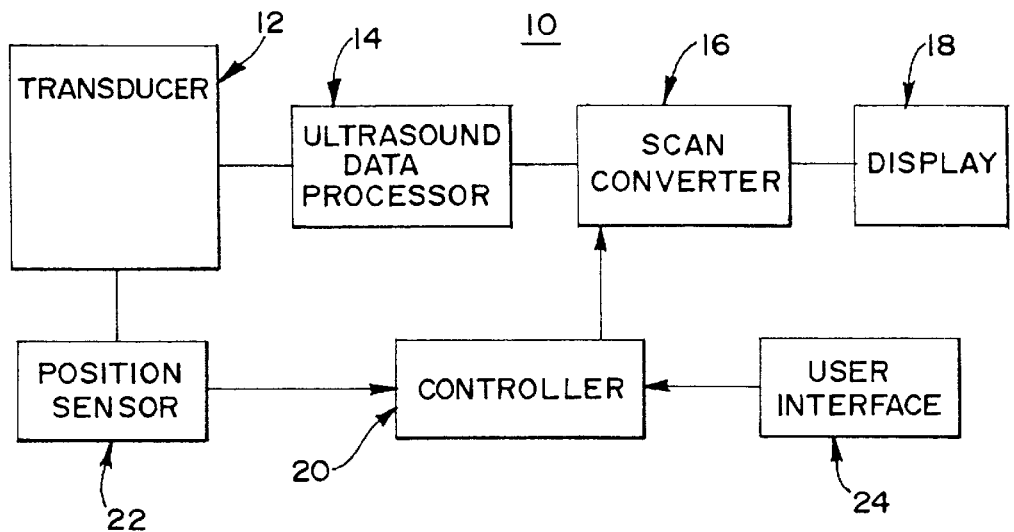
FIG. 1 is a block diagram of a medical diagnostic ultrasound system for scan plane orientation orientation.

FIG. 1 shows one preferred embodiment of a medical diagnostic ultrasound system for providing orientation information of the scan plane and associated image relative to the patient. The system 10 includes a transducer 12, and ultrasound data processor 14, a scan converter 16, a display 18 and a controller 20. The system 10 optionally includes a position sensor 22 and/or an user interface 24. In one preferred embodiment, the system 10 comprises a Sequoia®, Aspen™, or 128XP® medical diagnostic ultrasound system manufactured by Acuson. Other medical diagnostic ultrasound systems maybe used, such as systems provided by other manufactures.

The transducer 12 comprises a single element transducer, a linear array, a curved linear array, a 1.5 dimensional array, a two-dimensional array, a radial array, a transducer disclosed in U.S. Pat. Nos. 6,014,473 or 6,224,556 (Ser. No. 09/200,649 filed Nov. 25, 1998), the disclosures of which are incorporated herein by reference, or other transducer arrays. In one embodiment, the transducer 12 is adapted for use external to the patient, such as including a hand held housing or a housing for mounting to an external structure. In other embodiments, the transducer 12 is adapted for use internal to the body, such as arrays mounted within catheters or endocavity devices.

The transducer 12 is used to convert electrical signals into acoustic signals for scanning a region of the body. The transducer 12 also converts acoustic reflections in response to the scan into electrical signals. The region of the body scanned is a function of the type of transducer array. For example, a linear transducer array may scan a rectangular of square region of the body. As another example, a curved linear array may scan a pie shaped region of the body. Scans conforming to other geometrical regions or shapes within the body may be used.

The ultrasound data processor 14 comprises one or more of a general processor, a digital signal processor, application specific integrated circuits, logic devices, analog devices, other electrical components and combinations thereof for transmit and receive beam formation, filtering, signal processing and performing other processes for ultrasound image generation. The ultrasound data is output by the ultrasound data processor 14 to the scan converter 16.

The scan converter 16 comprises a general processor, a digital signal processor, an applications specific integrated circuit, a memory, analog devices or other components for formatting the ultrasound data from a polar coordinate format to a cartesian coordinate format. The scan converter 16 converts the ultrasound data for generation of an image on the display 18. In one preferred embodiment, the scan converter comprises an embodiment disclosed in U.S. Pat. No. 5,563,810, the disclosure of which is incorporated herein by reference. The scan converter 16 includes an image plane memory and a graphics memory. For example, the image plane memory stores ultrasound data for generating an image, and the graphics plane memory stores data providing various numerical vales and graphic displays. The data in the two memories are combined by the scan converter 16 for display on the display 18. The scan converter 16 outputs the converted ultrasound image data to the display 18.

The display 18 comprises a monitor, a CRT, a flat panel display or other display device for generating an ultrasound image. The display 18 is operable to display an ultrasound two-dimensional image representing the two-dimensional regions scanned in the body, graphical information, such as a generic representation of a body, and other information provided by the scan converter 16. The displays generated by the display 18 are discussed below.

The controller 20 comprises one or more general processors, digital signal processors, application specific integrated circuits or other logic devices for controlling the scan converter 16 and receiving inputs from the position sensor 22 and user interface 24. For example, the controller 20 comprises a system controller of an ultrasound system. The controller provides information to the scan converter 16 to control the orientation of the image. The controller 20 may also be operable to generate or control the generation of graphical information, such as wire frame representations of a portion of the body, graphical compasses labeled to indicate the position of the body, letter or numerical labels representing the position of the body relative to the image and other graphical information.

The user interface 24 comprises a keyboard, track ball, mouse, touch screen, graphical user interface, dedicated keys, software controlled keys, other input devices and combinations thereof for inputting information from a user to the system 10. The input information is provided to the controller 20.

The optional position sensor 22 comprises a magnetic position sensor, or other measurement devices for determining the positioning of the transducer 12 relative to the patient. Preferably, the magnetic positioner is used and comprises orthogonal coils placed on the transducer and in a nearby transmitter, such as the magnetic positioners manufactured by Biosense of New York or Ascension Technology of Burlington, Vt. By sequencing the transmitter transmission through the transmitter coils and measuring signals on each of the sensors coils, the location and orientation of the sensor coil is determined. Based on the position and orientation of the patient relative to the transmitter coils, the location and orientation of the transducer 12 is determined. In alternative embodiments, ultrasound data or other sources of information are used to determine the position or movement of the transducer 12.

Figure 2:
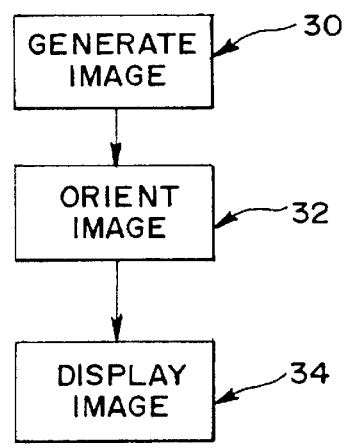
FIG. 2 is a flow chart representing one preferred embodiment of a method for scan plane orientation orientation.

FIG. 2 shows a flow chart of one preferred embodiment of the operation of this system 10 of FIG. 1. In act 30, an image is generated. The image is then oriented in act 32. The oriented image is then displayed in act 34.

In one embodiment, the ultrasound image is a two-dimensional image. The image is surrounded by an edge or a border designating the image from the display background. The border or edge may comprise a graphical line, graphical points (e.g. dashed line) or no graphical information other than the edge of the image.

The shape of the border or edge may be a function of the transducer 12. For example, a linear transducer provides for a rectangular or square border and associated image. A curved linear transducer, a sector transducer, or a Vector® wide view array transducer provide for a pie shaped border and image. The rectangular or square shaped image has four edges. A sector image has two substantially straight edges joining at an apex at one end and connecting by a curved edge at another end. A curved linear or Vector® image has similar edges to a sector image, but another straight or curved line, respectively, connects the straight edges on the top end rather than connecting at an apex or a point.

At least a point of one edge of the image and associated border corresponds to a position substantially adjacent to the transducer. For example, one edge of a linear formatted image, the apex of a sector shaped image, and the curved line on a Vector® image correspond to the face of the transducer. As used herein, substantially adjacent includes images and resulting edges that are spaced from the transducer. For example, the image may represent information spaced from the transducer starting at one centimeter to 20 centimeters. Other ranges maybe used. The edge of the image generally closest to the transducer represents the portion of the image substantially adjacent to the transducer. As another example, a section of an image may be selected for enlargement, such as a portion of the image spaced away from the transducer. When the enlarged section is displayed, the portion of the image or edge of the image generally closest to the transducer comprises the portion of the image that is substantially adjacent to the transducer.

The generated ultrasound image is oriented on the display as a function of the position of the transducer 12 or scan plane relative to the patient. The ultrasound image is displayed at an angle of rotation away from vertical on the display. A center of the edge corresponding to the position substantially adjacent to the transducer is oriented at an angle of rotation away from vertical. For example, a line orthogonal to the face of the transducer is displayed at an angle away from vertical on the display. The orthogonal line may be closer to a horizontal position than a vertical position. The orientation of the image is controlled so that the image is oriented away from a transducer up or a transducer down position.

In one embodiment for two-dimensional imaging, the image is displayed such that the scan plane and the display plane are parallel. A line perpendicular to the scan plane in the body is also perpendicular to the display. Orienting the image on the display comprises orienting the image at an angle of rotation within that common plane. Alternatively, the image is further oriented to appear as if in a plane that is not the display plane.

The controller 20 determines the orientation of the generated image relative to the patient or body being imaged. The orientation is determined as a function of the scan plane and associated orientation of the transducer with respect to the patient. The determination is either automatic or a function of input by a user. For manual orientation, the user operates the user interface 24. In response, the controller 20 determines the orientation. The user rotates the orientation of the image to any arbitrary angle using a track ball or other device on the user interface 24. The user visually determines the orientation of the transducer with respect to the patient and attempts to match that orientation on the display. Alternatively, the user orients the image on the display in a manner best suited for the user's medical analysis. In one embodiment, controls to flip the image left and right or up and down relative to the transducer position are also provided. The user orients the image in real-time with data acquisition or while reviewing previously stored images.

Automatic detection is performed in response to a position sensor 22 or some form of position estimation, such as based on ultrasound data.

Figure 8A:
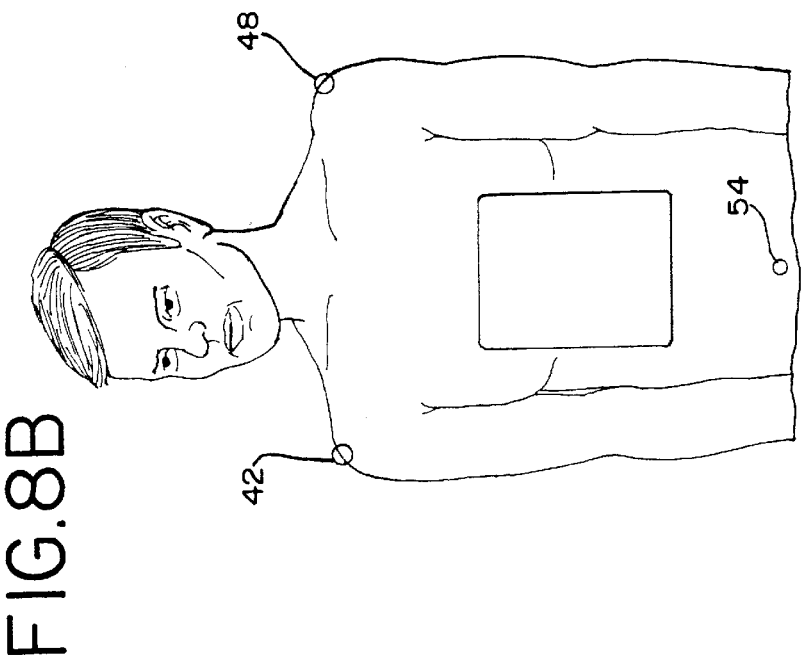
FIG. 8A is a flow chart representing one preferred embodiment for calibrating or otherwise determining an initial starting location of a transducer.
Figure 8B:
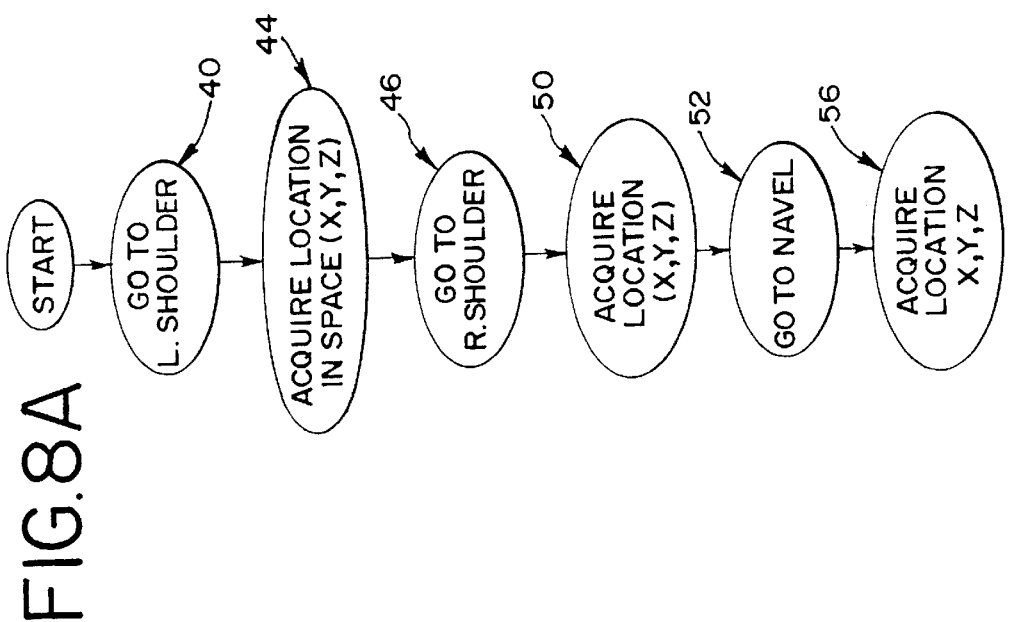
FIG. 8B is a graphical representation of a patient and locations on the patient used in the method described in FIG. 8A.

Referring to FIGS. 8A and 8B, a method for using the position sensor 22 to orient an image with respect to the body is shown. The position sensor 22 is mounted on the transducer 12, and the position of the transducer and the position sensor relative to known anatomical points on the patient being scanned are determined. For example, the patient's heart is imaged. In act 40, the position sensor 22 is placed on the left shoulder extremity as shown in FIG. 8B at point 42. The position of the position sensor 22 relative to another sensor is determined in act 44. In act 46, the position sensor 22 is repositioned to the right shoulder extremity shown in point 48 in FIG. 8B. The position of the position sensor 22 is then acquired in act 50. In act 52, the position sensor 22 is placed on the navel shown by position 54. The location of the position sensor 22 is then determined. The location of the points 42, 48 and 54 are determined in one embodiment using magnetic position sensors including a position sensor 22 on the transducer 12 and associated orthogonal magnetic coils positioned elsewhere to determine the spatial location of the position sensor 22.

The controller 20 uses information from the position sensor 22 to determine the position of the position sensor 22 and transducer 12 with respect to the known anatomical structure positions. Other automatic methods for determining a location of a scan plane and associated transducer 12 with respect to the patient maybe used. For example, the position of a catheter transducer within a body is measured as a function of the length of the catheter that has been inserted into the body and multiple measures of the curvature along the length of the catheter, such as using Wheatstone bridge circuits spaced periodically along the length of the catheter. In another embodiment, an initial position of the transducer 12 relative to the patient is determined. Further positioning is determined by calculating the movement of the transducer. In one embodiment, movement of the transducer 12 is determined as a function of the ultrasound data acquired by scanning the patient. Preferably, the transducer 12 includes at least two perpendicular arrays for tracking the movement of the transducer 12. For examples of tracking the movement of the transducer 12 using the acquired ultrasound data, see U.S. Pat. No. 6,014,473. Combinations of any of the automatic or manual methods discussed above maybe used for more accurate determination of the position of the transducer 12 and associated scan plane relative to the patient.

Figure 3A:
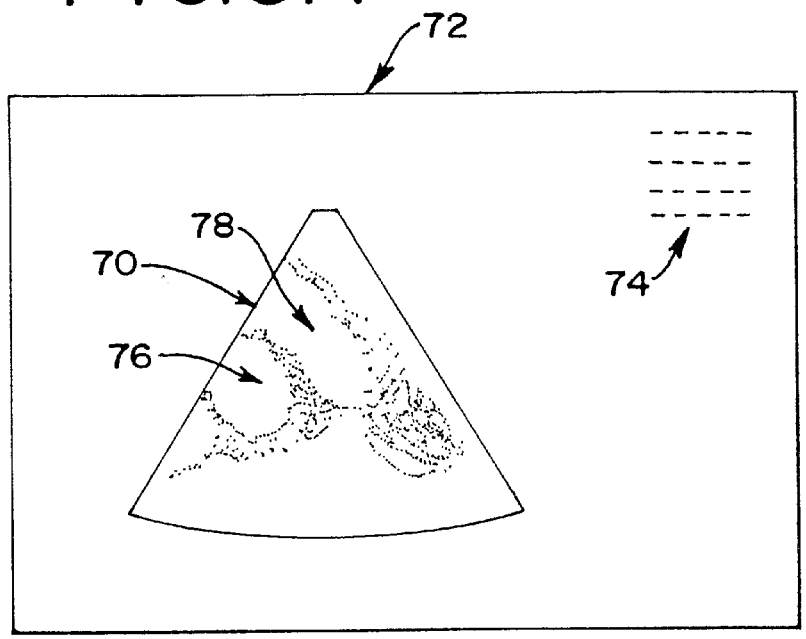
FIGS. 3A and 3B are graphical representations of one preferred embodiment showing an orientation of an image on a display.
Figure 3B:
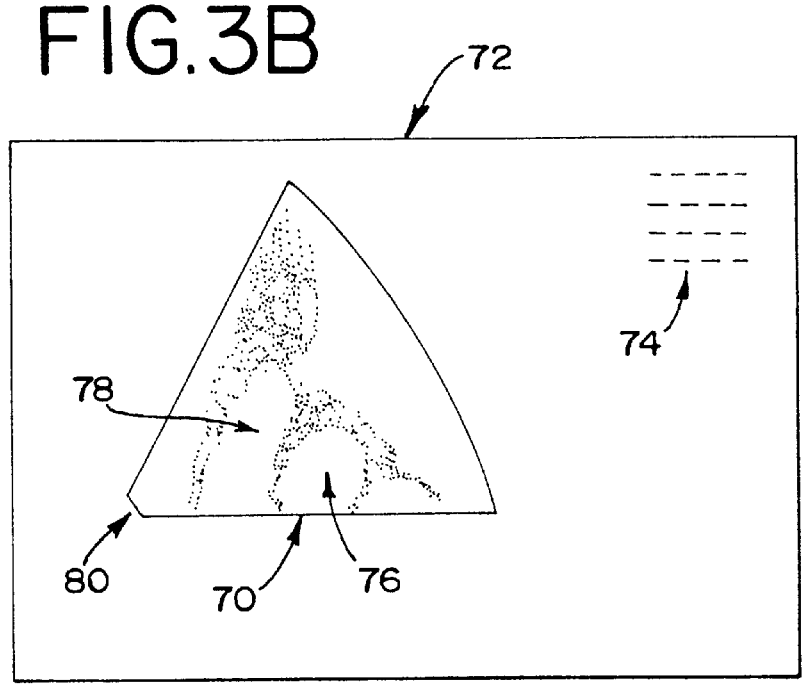

After the orientation of the image is determined, a display is generated that includes the image. For example, an image of the heart is generated as shown in FIGS. 3A and 3B. Both figures include an image 70 generated on a display 72. The display 72 also includes graphical information, such as system setting information at 74. The images include an area 76 associated with the pulmonary artery and an area 78 associated with the ascending aorta. In FIG. 3A, the image 70 is shown in a transducer up position where a line orthogonal to the face of the transducer is vertical on the display 72. The area 76 representing the pulmonary artery is shown in a substantially horizontal alignment with the area 78 representing the ascending aorta. In the FIG. 3B, the image 70 is oriented so that the area 78 is above and on the opposite side of the area 76 than was shown in FIG. 3A. This orientation of the image 70 more closely approximates the position of these internal structures relative to a standing patient. An edge 80 of the image 70 associated with or corresponding to a position of the transducer 12 (not shown) is oriented at an angle of rotation away from vertical on the display 72. A line orthogonal of the transducer is closer to a horizontal position than to a vertical position in this orientation. Other orientations maybe used as discussed above.

Figure 4A:
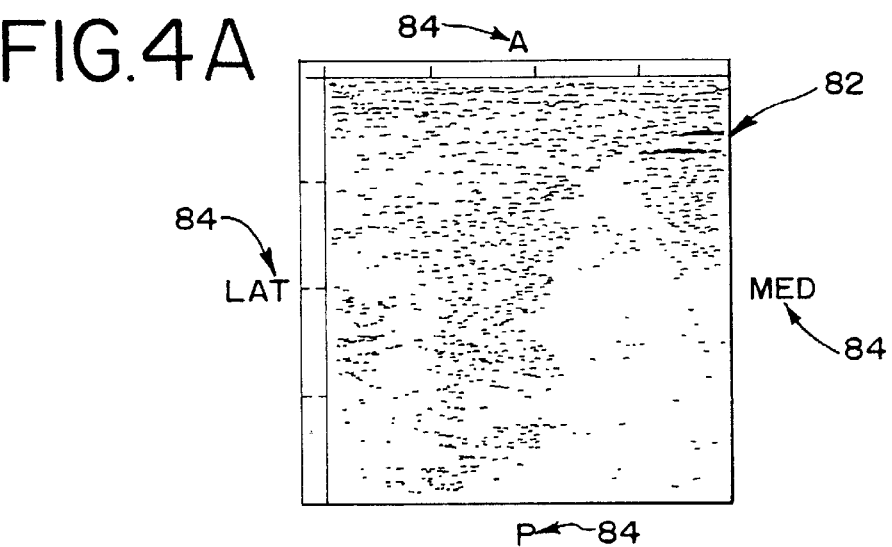
FIGS. 4A, 4B and 4C are graphical representations of one preferred embodiment for showing labels to provide orientation information of an image.
Figure 4B:
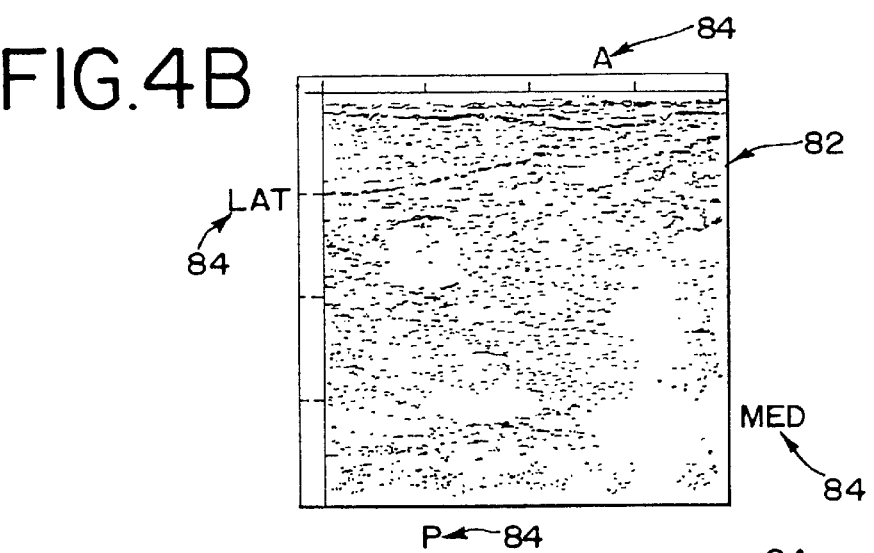
Figure 4C:
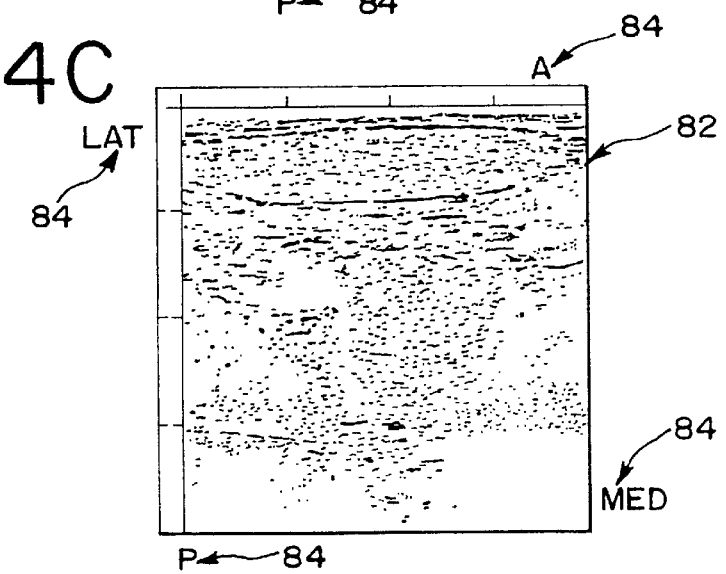
Figure 4D:
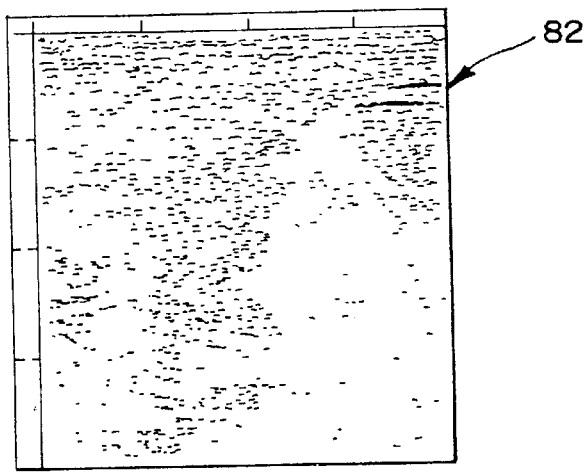
FIGS. 4D, 4E and 4F are graphical representations showing angular rotation represented by the labels of FIGS. 4A–4C.
Figure 4E:
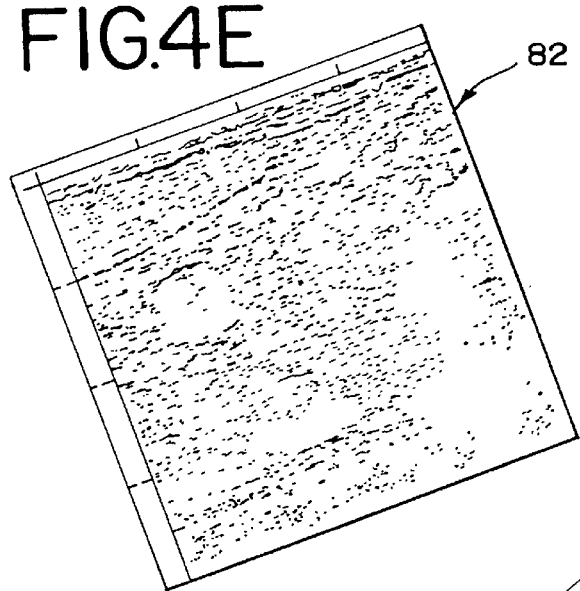
Figure 4F:
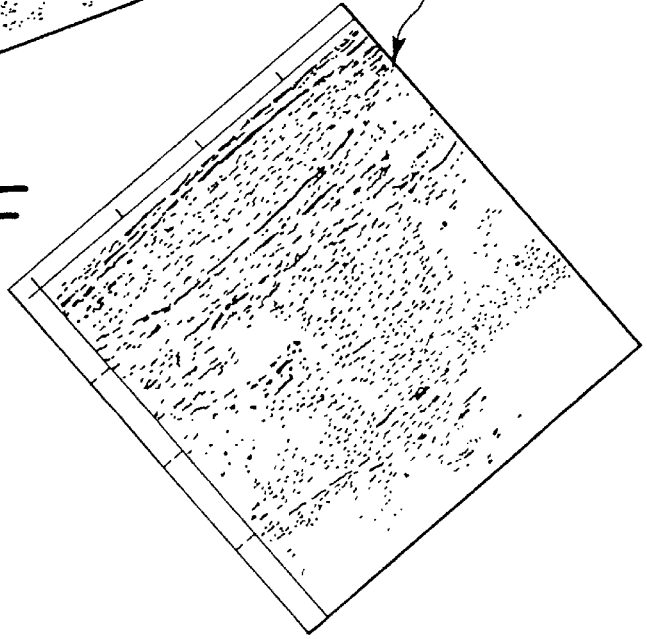

See also FIGS. 4D–4F.

As another example, a cross-section of the leg is imaged. The image is oriented in a transducer up position when the transducer 12 is on the top or anterior side of the leg. After the transducer 12 is rotated around to the side of the leg, the image also rotates so that the top of the leg stays at the top of the display.

In one embodiment, a two-dimensional image free of any three-dimensional representations or rendered images is provided, such as typically performed in real time diagnostic imaging. As shown in FIGS. 3A and 3B, a two-dimensional image free of any three-dimensional representations is displayed. In alternative embodiments, three-dimensional imaging or combinations of two and three-dimensional imaging maybe provided.

FIGS. 4A–4C show another technique to indicate the orientation of the scan plane relative to the patient. Reference labels 84 are placed around the image 82. The reference labels 84 indicate the direction of the scan plane relative to the 25 patient, such as A-indicating anterior, P-indicating posterior, Lat-indicating lateral Med-indicating medical. Other labels maybe used. As the scan plane changes orientation or is at a different orientation within the patient, the position of the labels 84 relative to the image 82 changes as shown in FIGS. 4B and 4C. FIGS. 4D through 4F correspond respectively to FIGS. 4A through 4C and indicate display of the image 82 corresponding to the orientation technique without labels as described above. In alternative embodiments, further label or numerical values maybe used to indicate the obliquity of the image 82 to a standard imaging plane, providing a three-dimensional positioning of the image 82 relative to the patient. And yet other embodiments, numerical values indicating an angle or distances of displacement are provided.

In one embodiment, the orientation of the image is combined with labeling as described above. For example, the descending aorta is imaged from the inferior vena cava (IVC). One possible presentation presents the image with the distal portion of the image on the right side of the screen, labeled with an L for the patient's left, with the superior portion on the top of the screen labeled with an S for superior and the inferior portion at the bottom of the screen, labeled with an I for inferior.

In one embodiment, the user manually enters labels indicating the position of the scan plane relative to the patient. For example, labels are provided in addition to orienting the image away from a vertical position.

In addition to the orientation of the transducer, an absolute position of the transducer relative to the patient or other reference point may be displayed. This information is either obtained from the system operator or from the position sensor 22.

In another embodiment, the position of the scan plane relative to the patient is indicated with a generic representation. Two and/or three-dimensional representations may be used. In alternative embodiments, the representation is generated as a function of a scan of the patient rather than as a generic representation. The generic representation is displayed with images in a transducer up or transducer down position or images oriented away from such vertical positioning.

Figure 5A:
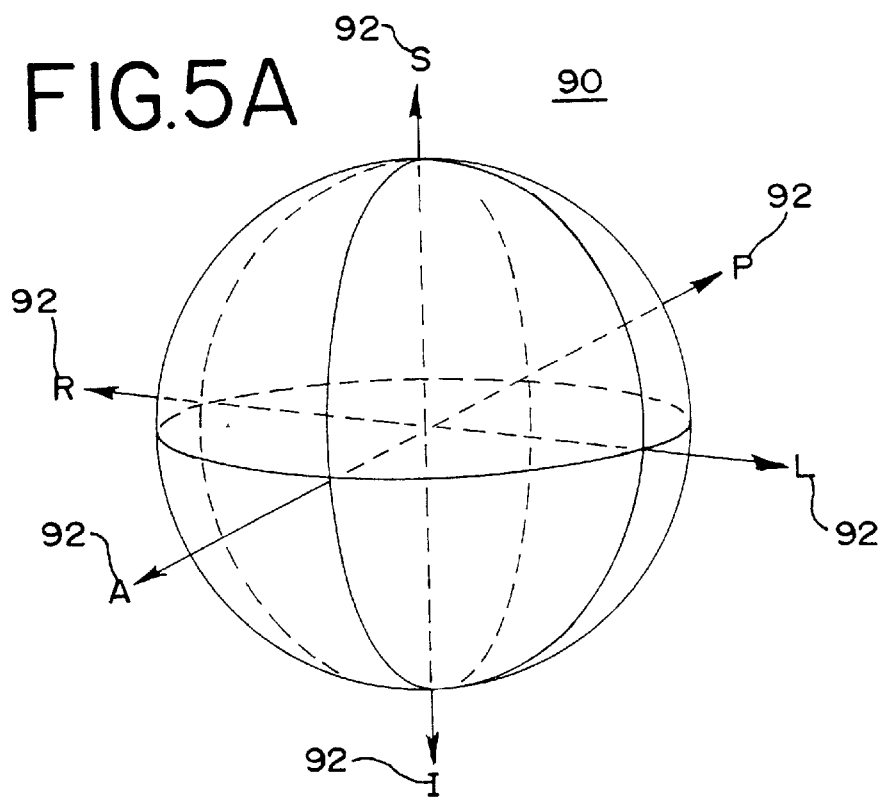
FIG. 5A is a graphical representation of one preferred embodiment of a generic compass display.
Figure 5B:
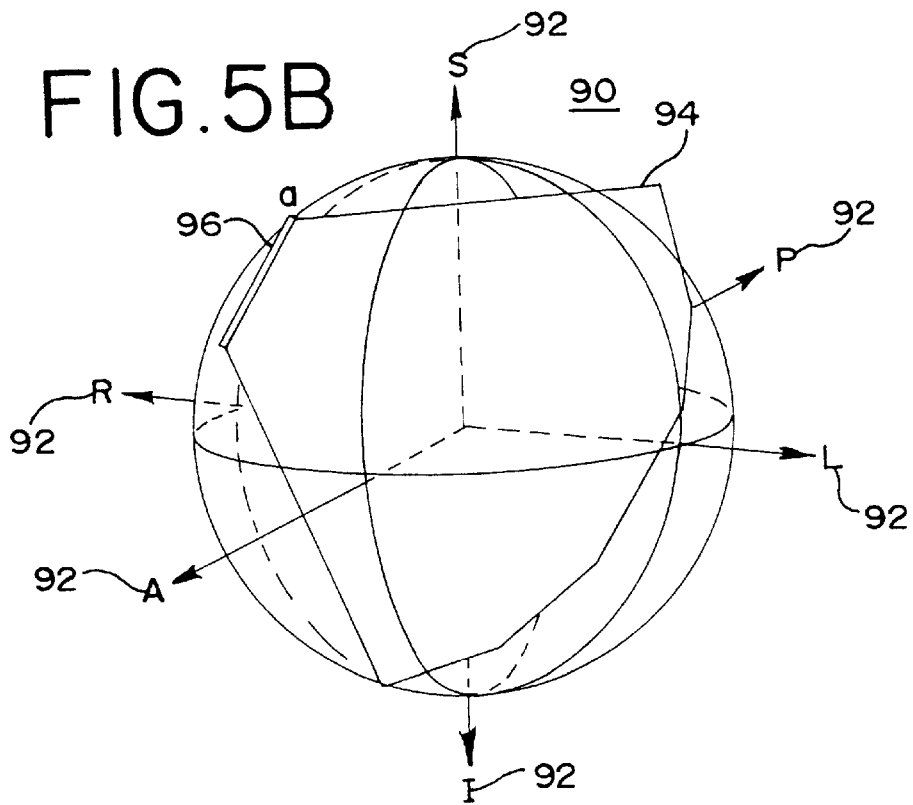
FIG. 5B is a graphical representation of one preferred embodiment for showing the location of a scan plane relative to the generic compass of FIG. 5A.

In one embodiment, a graphic on the screen indicating the orientation of the scan plane relative to a coordinate system based on the patient is generated as a generic representation. For example, FIGS. 5A and 5B show a generic representation 90 comprising a translucent sphere or graphical lines representing a sphere. Preferably, compass points or labels 92 are provided in conjunction with the generic representation. In one embodiment, the compass is labeled with S for superior, I for inferior, P for posterior, A for anterior, R for right and L for left to indicate the relative position of the patient with respect to the sphere. A generic scan plane representation or polygon 94 is graphically displayed within the sphere or generic representation 90. Preferably, the polygon 94 is shaped substantially similar to the image and actual scan plane. Preferably, the polygon 94 is displayed opaquely or semi opaquely. In one embodiment, the position of the transducer is indicated graphically by a line or other representation 96. In alternative embodiments, the position of the transducer is indicated by the shape of the polygon 94 as discussed above.

The image is either displayed adjacent to the graphical representation 90 or as part of the graphical representation 90. For example, the polygon 94 is rendered or textured map so that the image is displayed as part of the polygon 94. The image is positioned within the translucent generic graphical representation 90 to indicate the position of the scan plane relative to the patient.

In one embodiment, the generic representation represents at least a portion of the body. A two or three-dimensional representation maybe used, such as a representation of a heart chamber, a complete heart, an organ, the torso or the entire human body. In one embodiment, the representation is a wire frame or trace outline. More detailed generic representations maybe used, such as graphically rendered generic representations of the human body. For example, the digitized human representation provided by Transom Technologies, Inc. of Ann Arbor, Mich. is used (see for example the Jack 2.0 software).

The generic representation of the relative anatomy is stored by the controller 20. Preferably, the generic representation representing the body comprises a three-dimensional model capable of being manipulated with six degrees of freedom, such as three translation and three rotation degrees of freedom. In this embodiment, the three-dimensional model is automatically or manually scaleable as a function of the size of the image being acquired. The position and orientation of the scan plane is detected by the controller 20 in response to user input or automatically. Preferably, the controller 20 scales the generic representation as a function of the known scan plane depth, width and shape. For using a wire frame generic representation, the representation is rendered using open GL applications, but other rendering techniques maybe used such as the mathematical operations described by Foley et al in *Computer Graphics* published by Addison-Wesley, 1996.

Figure 6:
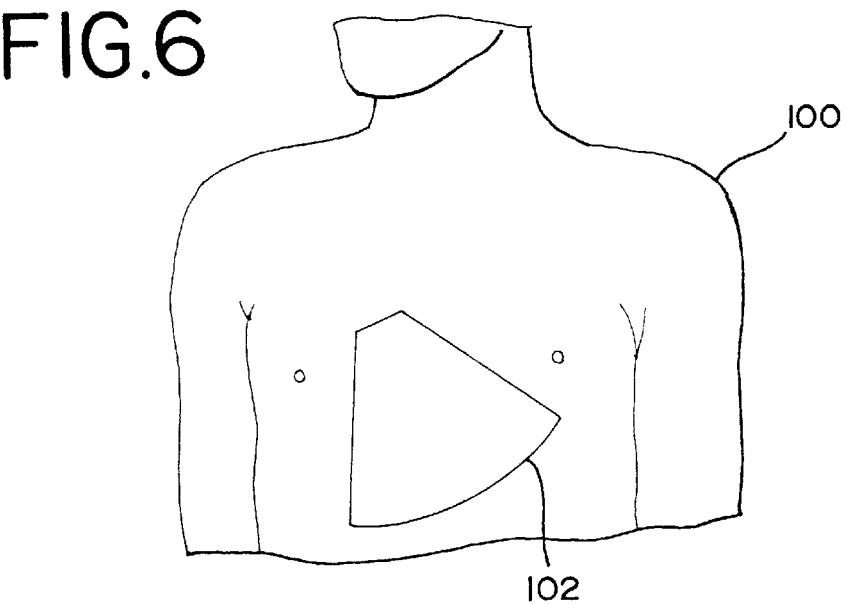
FIG. 6 is a graphical representation of one preferred embodiment showing the orientation of an image within a generic representation of a portion of a body.

The image is displayed in a fixed position where the generic representation is oriented relative to the image or the generic representation is displayed statically where the image is oriented with respect to the generic representation. For example, FIG. 6 shows a statically rendered wire frame generic representation of a portion of a torso at 100. The image 102 is oriented within the generic representation 100. The image 102 comprises a B-mode, M-mode, spectral doppler mode, flow mode, color mode, or other ultrasound image. The controller texture maps the ultrasound image unto a polygon defining the image plane within the anatomical wire frame using open GL commands. Preferably, the controller 20 includes a open GL accelerator, such as the ATI Rage Fury from Thornhill of Ontario, Canada.

In an alternative embodiment, the image is displayed adjacent to the generic representation 100. The position of the scan plane associated with the image is represented by a polygon 102 within the generic representation 100. The image is either displayed as an oriented image as discussed above or in the transducer up or transducer down position. The user refers to the generic representation and inserted polygon to determine the relative position of the scan plane within the patient.

Figure 7A:
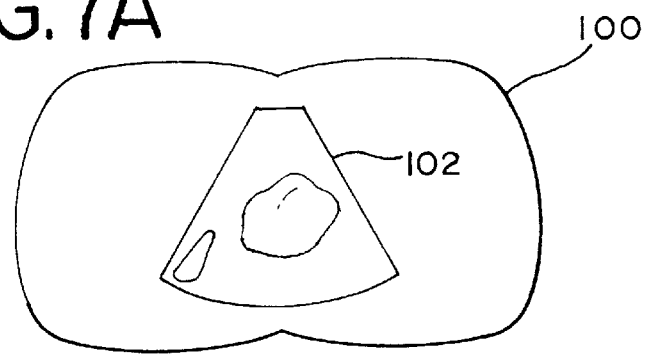
FIGS. 7A and 7B are graphical representations of one preferred embodiment for displaying a generic representation of a part of the body oriented geometrically with a substantially statically positioned two-dimensional ultrasound image.
Figure 7B:
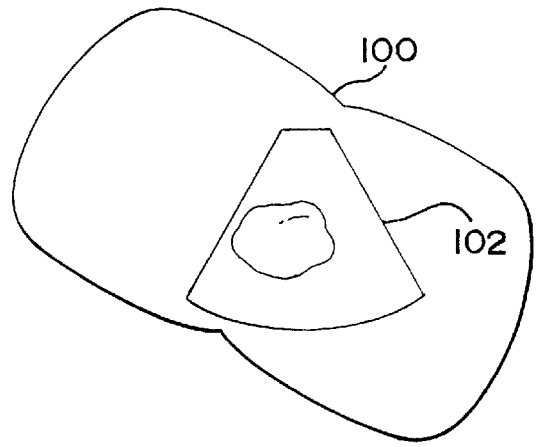

In alternative embodiments, the image is displayed statically while the generic representation is positioned relative to the static image. FIGS. 7A and 7B show a static image oriented in a transducer up position with a generic representation 100 oriented relative to the image 102. Alternatively, the image is displayed adjacent to the generic representation 100 and a polygon 102 is displayed within the generic representation 100. The image 102 remains static in the center of the display, such as in a conventional manner. The generic representation 100 is rotated, translated and scaled to correctly present the position of the image relative to the patient. For example, open GL API rendering using basic geometric calculations is used. As shown in FIGS. 7A and 7B, the graphical representation 100 comprises a wire frame representing the cross section of a patient's torso. In FIG. 7B, the scan plane is oriented at an angle away from the anterior and posterior axes of the patient.

Preferably, manual or automatic orientation of images or an indication of the orientation the scan plane within the patient is provided in real time ultrasound imaging. Additionally, image data is stored and an image is generated from the stored data at a later time. For example, the Aegis® Ultrasound Workstation by Acuson Corporation is used for generating the image. As another example, an auxiliary processor as disclosed in U.S. Pat. No. 6,159,150 (Ser. No. 09/196,207, filed Nov. 20, 1998), the disclosure of which is incorporated herein by reference, is used. Preferably, the user adjusts the orientation of the later generated image independent of any previous displays generated of that image. Content of the image may be more easily communicated to non-experts based on the orientation or positioning information.

While the invention has been described above by reference to various embodiments, it will be understood that many changes and modifications can be made without departing from the scope of the invention. For example, reference information aligned with the heart for heart imaging maybe used. The long axis of the heart is tilted approximately 30° to the patient's left. Similarly, other organs or body parts maybe used to determine the frame of reference and relative orientation or other information indicating a position of the scan plane relative to that frame of reference.

It is therefore intended that the foregoing detailed description be understood as an illustration of the presently preferred embodiments of the invention, and not as a definition of the invention. It is only the following claims, including all equivalents that are intended to define the scope of the invention.

What is claimed is:

1. A medical diagnostic ultrasound two-dimensional image representing a two-dimensional region within a body and comprising an edge having at least one point corresponding to a position substantially adjacent to a transducer, an improvement of the display comprising:

the image being oriented such that a direction orthogonal to a center of a face of the transducer is at an angle of rotation away from vertical on a display, the angle independent of a user selected reference point on a transducer-up or down image.

2. The display of claim 1 wherein the image is displayed such that a line perpendicular to a scan plane of the two-dimensional region of the body on the display is perpendicular to the display.

3. The display of claim 1 wherein the display is substantially free of three-dimensional representations rendered as a function of a scan of the body.

4. The display of claim 1 wherein the angle is responsive to a user selection.

5. The display of claim 1 wherein the angle is responsive to orientation information from a transducer position sensor.

6. The display of claim 1 further comprising a generic representation indicative of a position of the body.

7. The display of claim 6 wherein the generic representation comprises a three-dimensional compass graphic.

8. The display of claim 6 wherein the generic representation comprises a generic representation of at least a portion of the body.

9. The display of claim 6 further comprising a polygon positioned in the generic representation, the polygon comprising a same shape as the two-dimensional image wherein the generic representation is adjacent the two-dimensional image on the display.

10. The display of claim 6 wherein the two-dimensional image is positioned in the generic representation.

11. The display of claim 1 further comprising at least one displayed numerical value responsive to at least one of the orientation of the image and a position of the region within the body.

12. The display of claim 1 wherein the orientation of the image is adjustable.

13. The display of claim 1 wherein the image is responsive to stored ultrasound data and the orientation of the image are independent of previous displays generated as a function of the ultrasound data.

14. A medical diagnostic ultrasound system for displaying a two-dimensional image, the system comprising:
  an ultrasound transducer for scanning a two-dimensional region;
  a display operable to display an ultrasound two-dimensional image representing the two-dimensional region, the two-dimensional image having a portion corresponding to a position of the transducer relative to the two-dimensional image;
  a controller operative to orient the two-dimensional image as a function of an orientation of the transducer, the portion being at a position rotated away from vertical, the rotation of the position being independent of a user selected reference point on a transducer-up or down image.

15. The system of claim 14 further comprising a user input device, wherein the controller is operable to receive user input of the orientation of the transducer from the user input device.

16. The system of claim 14 further comprising:
  a position sensor operative to sense an orientation of the transducer;
  wherein the controller is operable to receive the orientation of the transducer from the position sensor.

17. The system of claim 16 wherein the position sensor comprises a magnetic position sensor connected with the transducer.

18. The system of claim 14 wherein the display is substantially free of three-dimensional representations rendered as a function of a scan of the body.

19. The system of claim 14 wherein the display is further operable to display a generic representation indicative of a position of the body.

20. The system of claim 19 wherein the generic representation comprises a three-dimensional compass graphic.

21. The system of claim 19 wherein the generic representation comprises a generic representation of at least a portion of the body.

22. The system of claim 19 wherein a polygon is positioned in the generic representation, the polygon comprises a same shape as the two-dimensional image, and the generic representation is adjacent the two-dimensional image on the display.

23. The system of claim 19 wherein the two-dimensional image is positioned in the generic representation.

24. The system of claim 14 wherein the controller and display comprise a remote workstation wherein the orientation of the two-dimensional image is response to input at the remote workstation.

25. The system of claim 14 further comprising a memory wherein the two-dimensional image is responsive to ultrasound data stored in the memory and the orientation of the image is independent of previous displays generated as a function of the ultrasound data.

26. A medical diagnostic ultrasound method for displaying a two-dimensional image, the method comprising the acts of:
  (a) generating a two-dimensional ultrasound image;
  (b) orienting the two-dimensional ultrasound image such that the image appears rotated from a transducer-up or down position as a function of a border of the image, the rotation independent of previous image data.

27. The method of claim 26 wherein (b) comprises positioning the image such that a center of an edge corresponding to a position adjacent to the transducer is oriented at an angle of rotation away from vertical on a display.

28. The method of claim 26 further comprising:
  (c) displaying the two-dimensional ultrasound image on a display, the display being substantially free of three-dimensional representations rendered as a function of a scan of the body.

29. The method of claim 26 further comprising:
  (c) inputting from the user the rotation of the image.

30. The method of claim 26 further comprising:
  (c) determining the rotation of the image as a function of a transducer position sensor.

31. The method of claim 26 further comprising:
  (c) generating a generic representation indicative of a position of the body.

32. The method of claim 31 wherein (c) comprises generating a three-dimensional compass graphic.

33. The method of claim 31 wherein (c) comprises generating a generic representation of at least a portion of the body.

34. The method of claim 31 further comprising:
  (d) generating a polygon positioned in the generic representation, the polygon comprising a same shape as the two-dimensional image.

35. The method of claim 31 wherein the two-dimensional image is positioned in the generic representation.

36. The method of claim 26 further comprising:
  (c) transferring ultrasound data to a remote workstation;
  wherein the image is generated as a function of the ultrasound data and the orientation is independent of any previous displays generated as a function of the ultrasound data.

37. A medical diagnostic ultrasound system for displaying a two-dimensional image, the system comprising:
  an ultrasound transducer probe adapted for use external to a patient to scan a two-dimensional region of the patient;

a display operable to display an ultrasound two-dimensional image representing the two-dimensional region wherein the display is free of three-dimensional representations rendered as a function of a scan of the patient; and a controller operative to orient the two-dimensional image as a function of an angle of the transducer probe to the patient, the orientation being independent of a user selected reference point in a previous image.

38. The system of claim 37 further comprising:
a user control wherein the orientation is responsive to user input of the angle.

39. The system of claim 37 further comprising:
a position sensor on the transducer probe wherein the orientation of the image is responsive to the position sensor.

40. The system of claim 37 wherein the controller is operative to orient the two-dimensional image such that a line on the image that is orthogonal to a face of the transducer is closer to a horizontal position than a vertical position.

41. A medical diagnostic ultrasound method for imaging a region of a body, the method comprising the acts of:
(a) ultrasonically scanning a region of interest in the body;
(b) monitoring an orientation of the region with respect to anatomical features of the body;
(c) displaying an ultrasound two-dimensional image responsive to the scan and a generic representation of at least a portion of the body wherein the image is geometrically aligned with the generic representation.

42. The method of claim 41 wherein (c) comprises rendering the two-dimensional image to align with a statically positioned generic representation.

43. The method of claim 42 wherein (c) comprises orienting the two-dimensional image such that a direction orthogonal to a center of a face of a transducer is oriented at an angle of rotation away from vertical.

44. The method of claim 41 wherein (c) comprises rendering the generic representation to align with a statically positioned two-dimensional image.

45. The method of claim 44 wherein (c) comprises orienting the statically positioned two-dimensional image in a transducer on top or bottom position.

46. The method of claim 41 further comprising:
(d) rendering a wire frame representation.

47. The method of claim 41 wherein (b) comprises monitoring a transducer probe orientation with a position sensor.

48. The method of claim 47 wherein (b) comprises monitoring with a magnetic position sensor.

49. The method of claim 41 wherein (b) comprises monitoring as a function of ultrasound data responsive to the scan.

50. The method of claim 41 wherein (b) comprises monitoring as a function of a user input estimation.

51. The method of claim 41 wherein (a) comprises scanning with a transducer array internal to the body.

52. The method of claim 51 wherein (a) comprises scanning with a transducer array mounted within a catheter.

53. The method of claim 41 wherein the at least a portion of the body is selected from the group consisting of: an organ, a portion of an organ, the heart, a portion of the heart, a portion of the torso and the torso.

54. A medical diagnostic ultrasound system for imaging a region of a body, the system comprising:
an ultrasound transducer for scanning a region of interest in a body;
a device operable to monitor an orientation of the region with respect to anatomical features of the body;
a display operable to display an ultrasound two-dimensional image responsive to information from the transducer and a generic representation of at least a portion of the body wherein the two-dimensional image is geometrically aligned with the generic representation.

55. The system of claim 54 further comprising a processor operable to render the two-dimensional image to align with a statically positioned generic representation on the display.

56. The system of claim 54 wherein the two-dimensional image is oriented such that a center of the edge corresponding to a position adjacent to the transducer is at an angle of rotation away from vertical.

57. The system of claim 54 further comprising a processor operable to render the generic representation to align with a statically positioned two-dimensional image on the display.

58. The system of claim 57 wherein the statically positioned two-dimensional image is oriented in a transducer on top or bottom position.

59. The system of claim 54 further comprising a processor operable to render a wire frame representation.

60. The system of claim 54 wherein the device comprises a position sensor.

61. The system of claim 60 wherein the device comprises a magnetic position sensor.

62. The system of claim 54 wherein the device comprises a processor operable to monitor as a function of ultrasound data responsive to the scan.

63. The system of claim 54 wherein the device comprises a user input device.

64. The system of claim 54 wherein the transducer comprises a transducer array adapted for use internal to the body.

65. The system of claim 64 wherein the transducer comprises a transducer array mounted within a catheter.

66. The system of claim 54 wherein the at least a portion of the body is selected from the group consisting of an organ, a portion of an organ, the heart, a portion o f the heart, a portion of the torso and the torso.

67. A medical diagnostic ultrasound two-dimensional image representing a two-dimensional region with in a body and comprising an edge having at least one point corresponding to a position substantially adjacent to a transducer, an improvement of the display comprising:
the image being oriented such that a direction orthogonal to a center of a face of the transducer is at an angle of rotation away from vertical on a display wherein the angle is responsive to a user selection of the angle.

68. The display of claim 67 wherein the orientation of the image is adjustable.

69. The display of claim 67 wherein the image is responsive to stored ultrasound data and the orientation of the image are independent of previous displays generated as a function of the ultrasound data.

70. The display of claim 67 wherein the transducer is adapted for insertion into a patient.

71. A medical diagnostic ultrasound system for displaying a two-dimensional image, the system comprising:
an ultrasound transducer for scanning a two-dimensional region;
a display operable to display an ultrasound two-dimensional image representing the two-dimensional region, the two-dimensional image having a portion corresponding to a position of the transducer relative to the two-dimensional image;

a controller operative to orient the two-dimensional image as a function of an orientation of the transducer, the portion being at a position rotated away from vertical; and a user input device;

wherein the controller is operable to receive user input of the orientation of the transducer from the user input device.

72. The system of claim 71 wherein the controller and display comprise a remote workstation wherein the orientation of the two-dimensional image is responsive to input at the remote workstation.

73. The system of claim 71 further comprising a memory wherein the two-dimensional image is responsive to ultrasound data stored in the memory and the orientation of the image is independent of previous displays generated as a function of the ultrasound data.

74. The system of claim 71 wherein the ultrasound transducer is adapted for insertion into a patient.

75. A medical diagnostic ultrasound two-dimensional image representing a two-dimensional region within a body and comprising an edge having at least one point corresponding to a position substantially adjacent to a transducer, an improvement of the display comprising:

the image being oriented such that a direction orthogonal to a center of a face of the transducer is at an angle of rotation away from vertical on a display;

wherein the image is responsive to stored ultrasound data and the orientation of the image are independent of previous displays generated as a function of the ultrasound data.

76. The display of claim 75 wherein the angle is responsive to a user selection.

77. The display of claim 75 wherein the transducer is adapted for insertion into the body.

78. A medical diagnostic ultrasound system for displaying a two-dimensional image, the system comprising:

an ultrasound transducer for scanning a two-dimensional region;

a display operable to display an ultrasound two-dimensional image representing the two-dimensional region, the two-dimensional image having a portion corresponding to a position of the transducer relative to the two-dimensional image;

a controller operative to orient the two-dimensional image as a function of an orientation of the transducer, the portion being at a position rotated away from vertical; and a memory wherein the two-dimensional image is responsive to ultrasound data stored in the memory and the orientation of the image is independent of previous displays generated as a function of the ultrasound data.

79. The system of claim 78 further comprising a user input device, wherein the controller is operable to receive user input of the orientation of the transducer from the user input device.

80. The system of claim 78 wherein the transducer is adapted for insertion into the body.

81. A medical diagnostic ultrasound two-dimensional image representing a two-dimensional region within a body and comprising an edge having at least one point corresponding to a position substantially adjacent to a transducer, an improvement of the display comprising:

the image being oriented such that a direction orthogonal to a center of a face of the transducer is at an angle of rotation away from vertical on a display;

wherein the transducer is adapted for insertion into a patient.

82. The display of claim 81 wherein the angle is responsive to a user selection.

83. The display of claim 81 wherein the image is responsive to stored ultrasound data and the orientation of the image are independent of previous displays generated as a function of the ultrasound data.

84. A medical diagnostic ultrasound system for displaying a two-dimensional image, the system comprising:

an ultrasound transducer adapted for insertion into a patient for scanning a two-dimensional region;

a display operable to display an ultrasound two-dimensional image representing the two-dimensional region, the two-dimensional image having a portion corresponding to a position of the transducer relative to the two-dimensional image; and a controller operative to orient the two-dimensional image as a function of an orientation of the transducer, the portion being at a position rotated away from vertical.

85. The system of claim 84 further comprising a user input device, wherein the controller is operable to receive user input of the orientation of the transducer from the user input device.

86. The system of claim 84 wherein the controller and display comprise a remote workstation wherein the orientation of the two-dimensional image is response to input at the remote workstation.

87. The system of claim 84 further comprising a memory wherein the two-dimensional image is responsive to ultrasound data stored in the memory and the orientation of the image is independent of previous displays generated as a function of the ultrasound data.

88. The system of claim 84 further comprising a position sensor connected with the ultrasound transducer.

89. A medical diagnostic ultrasound method for displaying a two-dimensional image, the method comprising the acts of:

(a) inserting an ultrasound transducer in a catheter into a target;

(b) generating a two-dimensional ultrasound image responsive to information from the ultrasound transducer, the two-dimensional ultrasound image being rectangular or pie shaped;

(c) orienting the two-dimensional ultrasound image such that a direction orthogonal to a center of a face of the transducer is at an angle of rotation away from vertical on the display; and (d) determining the angle as a function of information from a position sensor connected with the catheter.

* * * * *